United States Patent

Murata et al.

[11] Patent Number: 5,215,983
[45] Date of Patent: Jun. 1, 1993

[54] CARBAPENEM COMPOUNDS

[75] Inventors: Masayoshi Murata, Osaka; Hideo Tsutsumi, Toyonaka; Keiji Matsuda, Takatsuki, all of Japan

[73] Assignee: Fujisawa Pharmaceutical Co., Ltd., Osaka, Japan

[21] Appl. No.: 595,801

[22] Filed: Oct. 10, 1990

[30] Foreign Application Priority Data

Oct. 23, 1989 [GB] United Kingdom .......... 8923844

[51] Int. Cl.$^5$ .............. C07D 487/04; A61K 31/40
[52] U.S. Cl. .............. 514/210; 540/350; 540/310
[58] Field of Search .......... 540/350, 310; 514/210

[56] References Cited

U.S. PATENT DOCUMENTS

| | | | |
|---|---|---|---|
| 4,921,852 | 5/1990 | Murata et al. | 540/350 |
| 4,962,103 | 10/1990 | Sunagawa et al. | 540/350 |
| 4,983,596 | 1/1991 | Murata et al. | 540/350 |

FOREIGN PATENT DOCUMENTS

| | | |
|---|---|---|
| 0072710 | 2/1983 | European Pat. Off. |
| 0102239 | 3/1984 | European Pat. Off. |
| 0126587 | 11/1984 | European Pat. Off. |
| 0160391 | 11/1985 | European Pat. Off. |
| 0182213 | 5/1986 | European Pat. Off. |
| 0243686 | 11/1987 | European Pat. Off. |
| 0333175 | 9/1989 | European Pat. Off. |
| 0343499 | 11/1989 | European Pat. Off. |
| 0368259 | 5/1990 | European Pat. Off. |

*Primary Examiner*—Nicholas S. Rizzo
*Attorney, Agent, or Firm*—Oblon, Spivak, McClelland, Maier & Neustadt

[57] ABSTRACT

Novel carbapenem compounds of the formula:

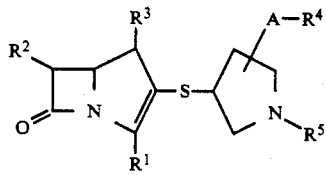

in which
$R^1$ is carboxy or protected carboxy,
$R^2$ is hydroxy(lower)alkyl or protected hydroxy(lower)alkyl,
$R^3$ is hydrogen or lower alkyl,
$R^4$ is unsaturated bicyclic heterocyclic group which may be substituted by suitable substituent(s),
$R^5$ is hydrogen or imino-protective group, and
A is lower alkylene, or pharmaceutically acceptable salts thereof.

Processes for their preparation and pharmaceutical compositions for the treatment of infectious diseases are also disclosed.

10 Claims, No Drawings

CARBAPENEM COMPOUNDS

FIELD OF THE INVENTION

The present invention relates to novel carbapenem compounds and pharmaceutically acceptable salts thereof.

More particularly, it relates to novel carbapenem compounds and pharmaceutically acceptable salts thereof, which have antimicrobial activity, to processes for the preparation thereof, to a pharmaceutical composition comprising the same, and to a use of the same as a medicament and in the treatment of infectious diseases in a human being or animal.

SUMMARY OF THE INVENTION

Accordingly, one object of the present invention is to provide novel carbapenem compounds and pharmaceutically acceptable salts thereof, which are highly active against a number of pathogenic microorganisms and are useful as antimicrobial agents.

Another object of the present invention is to provide processes for the preparation of novel carbapenem compounds and salts thereof.

A further object of the present invention is to provide a pharmaceutical composition comprising, as an active ingredient, said carbapenem compounds and pharmaceutically acceptable salts thereof.

Still further object of the present invention is to provide a use of said carbapenem compounds and pharmaceutically acceptable salts thereof as a medicament and in the treatment of infectious diseases caused by pathogenic microorganisms in a human being or animal.

DETAILED DESCRIPTION OF THE PREFERRED EMBODIMENTS

The object carbapenem compounds are novel and can be represented by the following general formula:

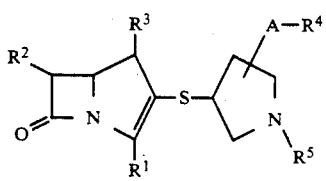
(I)

in which
$R^1$ is carboxy or protected carboxy,
$R^2$ is hydroxy(lower)alkyl or protected hydroxy(lower)alkyl,
$R^3$ is hydrogen or lower alkyl,
$R^4$ is unsaturated bicyclic heterocyclic group which may be substituted by suitable substituent(s),
$R^5$ is hydrogen, or imino-protective group, and
A is lower alkylene,
and pharmaceutically acceptable salts thereof.

Suitable pharmaceutically acceptable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.); a salt with a basic or acidic amino acid (e.g. arginine, aspartic acid, glutamic acid, etc.); an intermolecular or intramolecular quaternary salt; and the like.

The intermolecular quaternary salt can be formed when the unsaturated bicyclic heterocyclic group of $R^4$ in the compound (I) contains tertiary nitrogen atoms (e.g. 4,5,6,7-tetrahydropyrazolo[1,5-a]pyrimidinyl, 2,3-dihydro-imidazo[1,2-b]pyrazolyl, imidazo[1,2-b]-pyrazolyl,etc.), and suitable intermolecular quaternary salt may include 1-substituted-4,5,6,7-tetrahydropyrazolo-[1,5-a]pyrimidinio halide such as 1-(lower)-alkyl-4,5,6,7-tetrahydropyrazolo [1,5-a]pyrimidinio halide [e.g. 1-methyl-4,5,6,7-tetrahydropyrazolo[1,5-a]pyrimidinio iodide, 1-methyl-4,5,6,7-tetrahydropyrazolo[1,5-a]pyrimidinio chloride, 1-ethyl-4,5,6,7-tetrahydropyrazolo[1,5-a]pyrimidinio chloride, etc.], 5-substituted-2,3-dihydro-imidazo[1,2-b]pyrazolio halide such as 5-(lower)alkyl-2,3-dihydroimidazo [1,2-b]pyrazolio halide [e.g. 5-methyl-2,3-dihydroimidazo [1,2-b]pyrazolio iodide, 5-methyl-2,3-dihydro-imidazo[1,2-b]pyrazolio chloride, 5-ethyl-2,3-dihydro-imidazo[1,2-b]pyrazolio chloride, etc.]; 5-substituted-imidazo[1,2-b]pyrazolio halide such as 5-(lower)alkylimidazo[1,2-b]pyrazolio halide [e.g. 5-methylimidazo[1,2-b]pyrazolio iodide, 5-methylimidazo[1,2-b]pyrazolio chloride, 5-ethyl-2,3-dihydro-imidazo[1,2-b]pyrazolio chloride, etc.]; and the like.

The intramolecular salt can be formed when the unsaturated bicyclic heterocyclic group of $R^4$ in the compound (I) contains tertiary nitrogen atoms [e.g. 4,5,6,7-tetrahydropyrazolo[1,5-a]pyrimidinyl, 2,3-dihydro-imidazo[1,2-b]pyrazolyl, imidazo[1,2-b]-pyrazolyl, etc.) and $R^1$ is carboxy, and suitable intramolecular quaternary salt may include 1-substituted-4,5,6,7-tetrahydropyrazolo[1,5-a]pyrimidinio carboxylate such as 1-(lower)alkyl-4,5,6,7-tetrahydropyrazolo [1,5-a]pyrimidinio carboxylate [e.g. 1-methyl-4,5,6,7-tetrahydropyrazolo[1,5-a]pyrimidinio carboxylate, 1-ethyl-4,5,6,7-tetrahydropyrazolo [1,5-a]pyrimidinio carboxylate, etc.], 5-substituted-2,3-dihydro-imidazo[1,2-b]pyrazolio carboxylate such as 5-(lower)alkyl-2,3-dihydro-imidazo [1,2-b]pyrazolio carboxylate [e.g. 5-methyl-2,3-dihydro-imidazo[1,2-b]pyrazolio carboxylate, 5-ethyl-2,3-dihydro-imidazo[1,2-b]pyrazolio carboxylate, etc.]; 5-substituted-imidazo[1,2-b]pyrazolio carboxylate such as 5-(lower)alkylimidazo[1,2-b]pyrazolio carboxylate [e.g. 5-methylimidazo[1,2-b]pyrazolio carboxylate, 5-ethylimidazo[1,2-b]pyrazolio carboxylate, etc.]; and the like.

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.

According to the present invention, the object compound (I) or pharmaceutically acceptable salts thereof can be prepared by the processes as illustrated by the following reaction schemes.

Process 1:

Process 1 (continued)

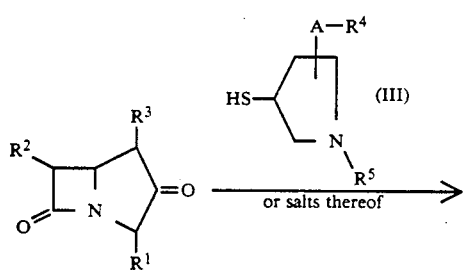

(II)
or a reactive derivative
at the oxo group thereof
or salts thereof

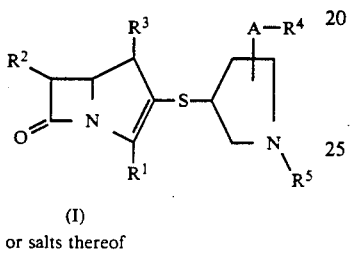

(I)
or salts thereof

Process 2:

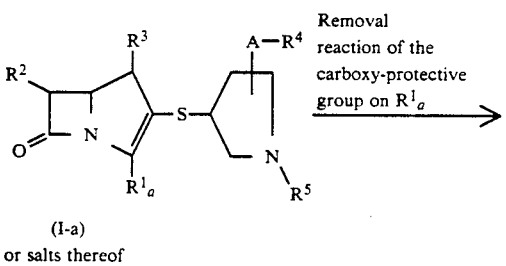

(I-a)
or salts thereof

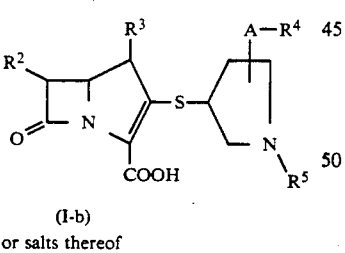

(I-b)
or salts thereof

Process 3:

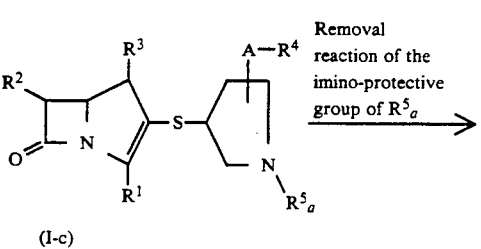

(I-c)
or salts thereof

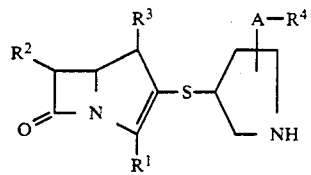

(I-d)
or salts thereof

Process 4:

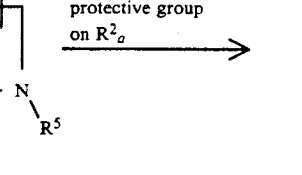

(I-e)
or salts thereof

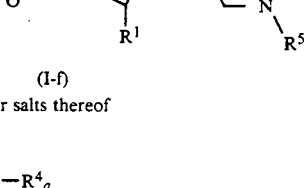

(I-f)
or salts thereof

Process 5:

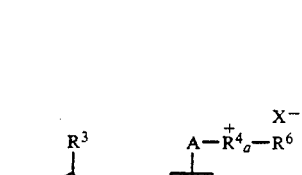

(I-g)
or salts thereof

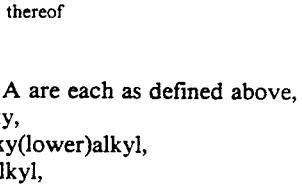

(I-h)
or salts thereof in which
$R^1$, $R^2$, $R^3$, $R^4$, $R^5$ and A are each as defined above,
$R^1_a$ is protected carboxy,
$R^2_a$ is protected hydroxy(lower)alkyl,
$R^2_b$ is hydroxy(lower)alkyl,
$R^4_a$ is unsaturated bicyclic heterocyclic group containing tertiary nitrogen atom, which may be substituted by suitable substituent(s),
$R^4_a$ is unsaturated polycyclic heterocyclic group containing quaternary nitrogen atom, which may be substituted by suitable substituent(s),
$R^5_a$ is imino-protective group, $R^6$ is lower alkyl, and X is an acid residue.

The compound (III) used in the Process 1 is new and can be prepared, for example, by the following methods or a conventional manner.

Method A:

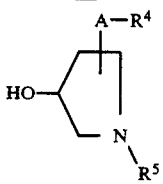

(IV)
or a reactive derivative
at the hydroxy group
thereof or salts thereof $\xrightarrow{R^7-SH \ (V)}$
or salts thereof

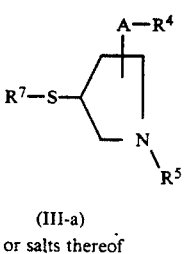

(III-a)
or salts thereof

Method B:

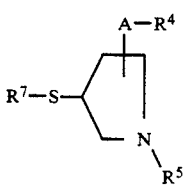

(III-a)
or salts thereof

Elimination reaction
of the mercapto-
protective group of
$R^7$

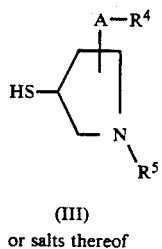

(III)
or salts thereof in which $R^4$, $R^5$ and A are each as defined above, and $R^7$ is mercapto-protective group.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable examples of the protected carboxy thus defined may be $C_2-C_4$ alkenyloxycarbonyl and phenyl(or nitrophenyl)($C_1-C_4$)alkoxycarbonyl, and the most preferable one may be 4-nitrobenzyloxycarbonyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1-C_4$)alkyl and the most preferable one may be 1-hydroxyethyl.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below; ar(lower)alkyl such as mono- or di- or triphenyl(lower)alkyl (e.g. benzyl, benzhydryl, trityl, etc.), etc.; trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.), etc.; and the like.

More preferable examples of "protected hydroxy(lower)alkyl thus defined may be [phenyl(or nitrophenyl)($C_1-C_4$)alkoxy]carbonyloxy($C_1-C_4$)alkyl and [tri($C_1-C_4$)alkylsilyl]oxy($C_1-C_4$)alkyl.

Suitable "lower alkyl" may include straight or branched alkyl such as methyl, ethyl, propyl, isopropyl, butyl, t-butyl, pentyl, hexyl, and the like, in which more preferable example may be $C_1$–$C_4$ alkyl and the most preferable one may be methyl.

Suitable unsaturated bicyclic heterocyclic group moieties characterized as "unsaturated bicyclic heterocyclic group which may be substituted by suitable substituent(s)", may include unsaturated bicyclic heterocyclic group containing at least one hetero-atom such as oxygen, sulfur or nitrogen atom.

Preferable unsaturated bicyclic heterocyclic groups may be:

unsaturated 7 to 12-membered, more preferably 8 or 9-membered, heterobicyclic group containing 1 to 4 nitrogen atom(s), for example, pyrazolopyrimidinyl (e.g. pyrazolo[1,5-a]pyrimidinyl, etc.), tetrahydropyrazolopyrimidinyl, (e.g. 4,5,6,7-tetrahydropyrazolo[1,5-a]pyrimidinyl, etc.), imidazopyrazolyl (e.g. imidazo[1,2-b]pyrazolyl, etc.), dihydroimidazopyrazolyl (e.g. 2,3-dihydro-imidazo[1,2-b]pyrazolyl, etc.), indolizinyl, isoindolyl, 3H-indolyl, indolyl, 1H-indazolyl, indolinyl, isoindolinyl, purinyl, 4H-quinolizinyl, isoquinolyl, quinolyl, phthalazinyl, naphthyridinyl (e.g. 1,8-naphtharidinyl, etc.), quinoxalinyl, quinazolinyl, cinnolinyl, pteridinyl, pyradinopyridazinyl (e.g. pyrazino[2,3-d]pyridazinyl, etc.), imidazotriazinyl (e.g. imidazo[1,2-b][1,2,4]triazinyl, etc.), etc.;

unsaturated 7 to 12-membered, more preferably 8 or 9-membered, heterobicyclic group containing 1 to 3 oxygen atom(s), for example, benzofuranyl (e.g. benzo[b]furanyl, etc.), isobenzofuranyl, chromenyl (e.g. 2H-chromenyl, etc.), isochromanyl, chromanyl, benzoxepinyl (e.g. 3-benzoxepinyl, etc.), cyclopentapyranyl (e.g. cyclopenta[b]pyranyl, etc.), furopyranyl (e.g. 2H-furo-[3,2-b]pyranyl, etc.), etc.;

unsaturated 7 to 12-membered, more preferably 8 or 9-membered, heterobicyclic group containing 1 to 3 sulfur atom(s), for example, dihydrodithianaphthalenyl (e.g. 4H-1,3-dithianaphthalenyl, etc.), dithianaphthalenyl (e.g. 1,4-dithianaphthalenyl, etc.), etc.;

unsaturated 7 to 12-membered, more preferably 8 or 9-membered, heterobicyclic group containing 1 to 3 nitrogen atom(s) and 1 to 2 oxygen atom(s), for example, dioxoloimidazolyl (e.g. 4H-1,3-dioxolo[4,5-d]imidazolyl, etc.), benzoxazinyl (e.g. 4H-3,1-benzoxazinyl, etc.), pyridooxazinyl (e.g. 5H-pyrido[2,3-d]-oxazinyl, etc.), pyrazoloxazolyl (e.g. 1H-pyrazolo[4,3-d]oxazolyl, etc.), etc.;

unsaturated 7 to 12-membered, more preferably 8 or 9-membered, heterobicyclic group containing 1 to 3 nitrogen atom(s) and 1 to 2 sulfur atom(s), for example, imidazothiazolyl (e.g. imidazo[2,1-b]thiazolyl, 4H-imidazo[4,5-b]thiazolyl, etc.), dithiadiazaindanyl (e.g. 2,3-dithia-1,5-diazaindanyl, etc.), etc;

unsaturated 7 to 12-membered, more preferably 8 or 9-membered, heterobicyclic group containing 1 to 2 oxygen atom(s) and 1 to 2 sulfur atom(s), for example, thienofuranyl (e.g. thieno[2,3-b]furanyl, etc.), etc;

unsaturated 7 to 12-membered, more preferably 8 or 9-membered, heterobicyclic group containing a nitrgen atom, a oxygen atom and a sulfur atom, for example, oxathiolopyrrolyl (e.g. 4H[1,3]-oxathiolo[5,4-b]pyrrolyl, etc.), etc.; and the like, wherein said heterocyclic group may be substituted by one or more, preferably one to three suitable substituent(s) such as oxo; carboxy(lower)alkyl, which is the aforementioned lower alkyl group substituted by carboxy; protected carboxy(lower)alkyl, which is the carboxy(lower)alkyl as mentioned above, in which the carboxy group is protected by a suitable carboxy-protective group to form so-called "esterified carboxy" as mentioned above; amino; protected amino in which the amino-protective group may be the same as those for the imino-protective group as mentioned below; lower alkylamino (e.g. methylamino, ethylamino, propylamino, isopropylamino, butylamino, hexylamino, etc.); ureido(lower)alkyl (e.g. ureidomethyl, ureidoethyl, ureidopropyl, ureidohexyl, etc.); carbamoyl; carbamoyl(lower)alkyl (e.g. carbamoylmethyl, etc.); lower alkyl as mentioned above; lower alkanoyl(lower)alkyl (e.g. acetylmethyl, etc.); amino(lower)alkyl (e.g. aminomethyl, aminoethyl, aminopropyl, aminobutyl, aminohexyl, etc.); protected amino(lower)alkyl, which is the amino(lower)alkyl group as mentioned above, in which the amino group is protected by a conventional amino-protective group such as those for the imino-protective group as mentioned below; hydroxy(lower)alkyl and protected hydroxy(lower)alkyl as mentioned above; azido(lower)alkyl (e.g. azidomethyl, azidoethyl, azidopropyl, azidohexyl, etc.); halo(lower)alkyl (e.g. chloromethyl, bromomethyl, iodoethyl, bromopropyl, bromohexyl, etc.); and the like. And further in case that said heterocyclic group is imidazolyl, pyrazolyl or imidazolinyl, the imino-moiety(ies) thereof may be protected by conventional imino-protective group(s) as mentioned below.

Preferable examples of unsaturated bicyclic heterocyclic groups which may be substituted by suitable substituent(s) may be:

tetrahydropyrazolopyrimidinyl (e.g. 4,5,6,7-tetrahydropyrazolo [1,5-a]pyrimidin-4-yl, etc.), dihydro-imidazopyrazolyl (e.g. 2,3-dihydro-imidazo[1,2-b]pyrazol-1-yl, etc.), and imidazopyrazolyl (e.g. imidazo[1,2-b]pyrazol-1-yl, etc.).

Suitable groups characterized as "unsaturated bicyclic heterocyclic group containing tertiary nitrogen atom, which may be substituted by suitable substituent(s)" may be "unsaturated bicyclic heterocyclic group which may be substituted by suitable substituent(s)" as mentioned above, in which said heterocyclic group contains a tertiary nitrogen atom.

Preferable examples of unsaturated bicyclic heterocyclic groups containing tertiary nitrogen atoms, which may be substituted by suitable substituent(s) may be:

tetrahydropyrazolopyrimidinyl (e.g. 4,5,6,7-tetrahydropyrazolo [1,5-a]pyrimidin-4-yl, etc.), dihydro-imidazopyrazolyl (e.g. 2,3-dihydro-imidazo[1,2-b]pyrazol-1-yl, etc.), and imidazopyrazolyl (e.g. imidazo[1,2-b]pyrazol-1-yl, etc.).

Suitable "unsaturated bicyclic heterocyclic group containing quaternary nitrogen atom, which may be substituted by suitable substituent(s)" may be "unsaturated bicyclic heterocyclic group containing tertiary nitrogen atom, which may be substituted by suitable substituent[s]", in which the tertiary nitrogen atom is substituted by suitable substituent(s) such as lower alkyl to form tertiary nitrogen atom.

Preferable examples of unsaturated bicyclic heterocyclic groups containing quaternary nitrogen atoms, which may be substituted by suitable substituent(s) may be:

1-substituted-tetrahydropyrazolopyrimidinio (e.g. 1-substituted-4,5,6,7-tetrahydro-4-pyrazolo[1,5-a]pyrimidinio, etc.), 5-substituted-dihydro-imidazopyrazolio (e.g. 5-substituted-2,3-dihydro-1-imidazo[1,2-b]pyrazolio, etc.), and 5-substituted-imidazopyrazolio (e.g. 5-substituted-1-imidazo [1,2-b]pyrazolio, etc.).

Suitable "imino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroaralkoxycarbonyl(e.g. nitrobenzyloxycarbonyl, etc.), and the like.

More preferable example of "imino-protective group" thus defined may be $C_2$–$C_4$ alkenyloxycarbonyl and phenyl(or nitrophenyl)($C_1$–$C_4$)alkoxycarbonyl and the most preferable one may be 4-nitrobenzyloxycarbonyl.

Suitable "lower alkylene" may include straight or branched alkylenes such as methylene, ethylene, trimethylene, tetramethylene, pentamethylene, hexamethylene, methylmethylene, ethylethylene, propylene, and the like, in which more preferable example may be $C_1$–$C_4$ alkylene and the most preferable one may be methylene.

Suitable "acid residue" may include an inorganic acid residue such as azido, halogen (e.g. chlorine, bromine, fluorine or iodine), and the like, an organic acid residue such as acyloxy (e.g. benzenesulfonyloxy, tosyloxy, methanesulfonyloxy, etc.), and the like, in which more preferable example may be halogen and the most preferable one may be iodine.

The processes for the preparation of the object compound (I) of the present invention are explained in detail in the following.

(1) Process 1:

The compound (I) or salts thereof can be prepared by reacting the compound (II) or a reactive derivative at the oxo group thereof or salts thereof with the compound (III) or salts thereof.

Suitable salts of the compound (II) may be salts with bases such as those given for the compound (I).

The reactive derivative at the oxo group of the compound (II) can be represented by the following formula (II'), which is preferably used in this reaction and can be prepared by reacting the compound (II) or salts thereof with an acylating agent.

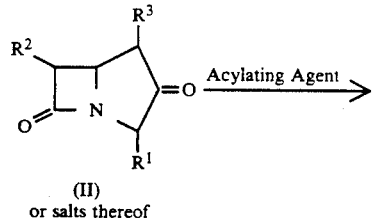

(II)
or salts thereof

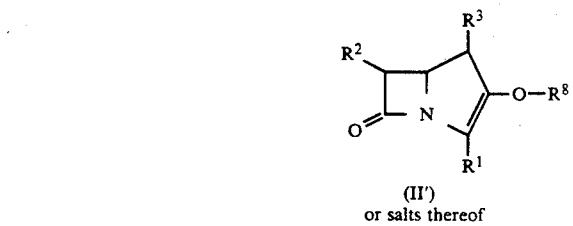

(II')
or salts thereof in which
$R^1$, $R^2$ and $R^3$ are each as defined above, and
$R^8$ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower)alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compound [e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl) carbodiimide, etc.]; N,N'-carbonyldiimidazole, N,N'-carbonylbis(2-methylimidazole); keteneimine compound (e.g. pentamethyleneketene-N-cyclohexylimine, diphenylketene-N-cyclohexylimine, etc.); ethoxyacetylene; 1-alkoxy-1-chloroethylene; ethyl biphosphate; isopropylpolyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; and the like.

This acylation reaction may be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compound [e.g. pyridine, picoline, lutidine, N,N-di(lower)alkylaminopyridine such as N,N-dimethylaminopyridine, etc.], quinoline, N-lower alkylmorpholine (e.g. N-methylmorpholine, etc.), N,N-di(lower)alkylbenzylamine (e.g. N,N-dimethylbenzylamine, etc.), alkali metal alkoxide (e.g. sodium methoxide, sodium ethoxide, potassium butoxide, etc.), and the like.

The reaction temperature of this acylation reaction is not critical and the reaction is usually carried out under from cooling to warming.

With regard to the compound (II), it is to be noted that the 3,7-dioxo-1-azabicyclo[3.2.0]heptane ring system of the following formula (IIA) is well known to lie to tautomeric relation with the 3-hydroxy-7-oxo-1-azabicyclo[3.2.0]hept-2-ene ring system of the following formula (IIB), and accordingly, it is to be understood that both of these ring systems are substantially the same.

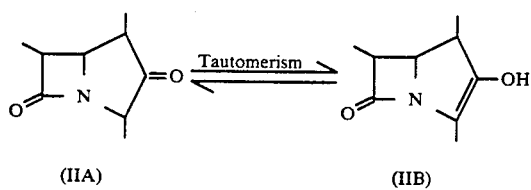

(IIA)                    (IIB)

The compound (II') or salts thereof can be used with or without isolation for the subsequent reaction with the compound (III) or salts thereof.

Suitable salts of the compound (III) may be the same as those for the compound (I) and silver salt.

The reaction of the compound (II) or its reactive derivative or salts thereof with the compound (III) or salts thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming.

(2) Process 2 :

The compound (I-b) or salts thereof can be prepared by subjecting the compound (I-a) or salts thereof to removal reaction of the carboxy-protective group on $R^1{}_a$.

Suitable salts of the compounds (I-a) and (I-b) may be the same as those for the compound (I).

The present reaction is usually carried out by a conventional method such as hydrolysis, reduction, and the like.

(i) Hydrolysis :

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction :

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

When catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is the allyl group, it can be deprotected by hydrogenolysis using a palladium compound.

Suitable palladium compounds used in this reaction may be palladium on carbon, palladium hydroxide on carbon, palladium chloride, a palladium-ligand complex such as tetrakis(triphenylphosphine)palladium(0), bis(dibenzylideneacetone)palladium(0), di[1,2-bis(diphenyl phosphino)ethane]palladium(0), tetrakis(triphenyl phosphite)palladium(0), tetrakis(triethyl phosphite)palladium (0), and the like.

The reaction can preferably be carried out in the presence of a scavenger of allyl group generated in situ. such as amine (e.g. morpholine, N-methylaniline, etc.), an activated methylene compound (e.g. dimedone, benzoyl acetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethyamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be removed.

The present process includes within the scope thereof a case that the hydroxy- and/or carboxy- and/or amino-protective group(s) on $R^2$ and/or $R^4$, and/or imino-protective group of $R^5$, and/or additional carboxy-protective group are removed at the same time during the reaction.

(3) Process 3 :

The compound (I-d) or salts thereof can be prepared by subjecting the compound (I-c) or salts thereof to removal reaction of the imino-protective group on $R^5{}_a$.

Suitable salts of the compounds (I-c) and (I-d) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy- and/or amino-protective group(s) on $R^1$ and/or $R^2$ and/or $R^4$, and/or additional carboxy-protective group are removed at the same time during the reaction.

(4) Process 4 :

The compound (I-f) or salts thereof can be prepared by subjecting the compound (I-e) or salts thereof to removal reaction of the hydroxy-protective group on $R^2{}_a$.

Suitable salts of the compounds (I-e) and (I-f) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy- and/or hydroxy- and/or amino-protective group(s) on $R^1$ and/or $R^4$, and/or the imino-protective group of $R^5$, and/or additional carboxy-protective group are removed at the same time during the reaction.

(5) Process 5 :

The compound (I-h) or salts thereof can be prepared by reacting the compound (I-g) or salts thereof with the compound (IV).

Suitable salts of the compounds (I-g) and (I-h) may be the same as those for the compound (I).

This reaction is usually carried out in a conventional solvent which does not adversely influence the reaction such as water, dioxane, tetrahydrofuran, acetone, acetonitrile, etc., or a mixture thereof.

The reaction temperature is not critical, and the reaction is usually carried out under from cooling to warming.

Methods A and B for preparing the new starting compound (III) or salts thereof are explained in detail in the following.

(A) Method A

The compound (III-a) or salts thereof can be prepared by reacting the compound (IV) or a reactive derivative at the hydroxy group thereof or salts thereof with the compound (V) or salts thereof.

Suitable salts of the compounds (III-a), (IV) may be the same as those for the compound (I).

Suitable salts of the compound (V) may be salts with bases such as those given for the compound (I).

Suitable reactive derivative at the hydroxy group of the compound (IV) may include a conventional one such as halide (e.g. chloride, bromide, iodide, etc.), sulfonate (e.g. methanesulfonate, benzenesulfonate, toluenesulfonate, etc.), and the like, in which more preferable example may be sulfonate.

The starting compound (IV) of this method is new and can be prepared by the methods described in the Preparations mentioned below.

Preferable example of the compound (V) may be ar(lower)alkanethiol such as mono- or di- or triphenyl(lower)alkanethiol (e.g. phenylmethanethiol, diphenylmethanethiol, triphenylmethanethiol, etc.), thio(lower)alkanoic S-acid (e.g. thioacetic S-acid, etc.) or salts thereof, thioarenoic S-acid or salts thereof (e.g. thiobenzoic S-acid, etc.), and the like, in which more preferable example may be triphenyl($C_1$-$C_4$)alkanethiol, thio($C_1$-$C_4$)alkanoic S-acid or alkali metal salts thereof and thio($C_6$-$C_{10}$)arenoic S-acid or alkali metal salts thereof, and the most preferable one may be triphenylmethanethiol, thioacetic S-acid and potassium thioacetate.

In case that the compound (V) may be ar(lower)alkanethiol, the starting compound (IV) of the present reaction is preferably used in the form of its reactive derivative at the hydroxy group, and in such a case, this reaction is usually carried out in the presence of an organic or inorganic base such as those exemplified in the explanation of Process 2.

In case that suitable example of compound (V) may be thio(lower)alkanoic S-acid or thioarenoic S-acid, this exaction is preferably carried out in the presence of a conventional condensing agent such as combination of triarylphosphine (e.g. triphenylphosphine, etc.) and di(lower)alkyl azodicarboxylate (e.g. diethyl azodicarboxylate, etc.).

This reaction is usually carried out in a conventional solvent which does not adversely influence the reaction such as dichloromethane, methanol, ethanol, propanol, pyridine, N,N-dimethylformamide, 4-methyl-2-pentanone, tetrahydrofuran, etc., or a mixture thereof.

The reaction temperature is not critical and the reaction is usually carried out under from cooling to warming.

In this method, the configuration on the carbon atom substituted with the hydroxy group of the compound (IV) is inverted in the compound (III-a).

(B) Method B

The compound (III) or salts thereof can be prepared by subjecting the compound (III-a) or salts thereof to elimination reaction of the mercapto-protective group.

This elimination reaction can be carried out by a conventional method as described below, which can be selected according to the kind of mercapto-protective group to be eliminated.

In case that the protective groups may be ar(lower)alkyl group, it can generally be eliminated by treating, for example, with a silver compound (e.g. silver nitrate, silver carbonate, etc.).

The reaction with the silver compound as stated above is preferably carried out in the presence of an organic base (e.g. pyridine, etc.).

The resultant silver salt of compound (III) can be transformed into its alkali metal salt, if necessary, by reacting with alkali metal halide (e.g. sodium iodide, potassium iodide, etc.).

Further, in case that the protective groups may be acyl group, it can generally be eliminated by solvolysis such as hydrolysis using an acid or base, alcoholysis using a base, and the like.

Suitable acid or base used in these reactions may be the same such as those given in the explanation of hydrolysis of the Process 2.

The hydrolysis is usually carried out in a conventional solvent which does not adversely influence the reaction such as water, alcohol (e.g. methanol, ethanol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, and the like.

The reaction temperature is not critical and the reaction is usually carried out under from cooling to warming.

The object compounds (I), (I-b), (I-d), (I-f) and (I-h) obtained according to the Processes 1 to 5, can be isolated and purified in a conventional manner, for example, extraction, precipitation, fractional crystallization, recrystallization, chromatography, and the like.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

In the present invention, the object compound (I) possessing more potent antimicrobial activity can be represented by the following formula:

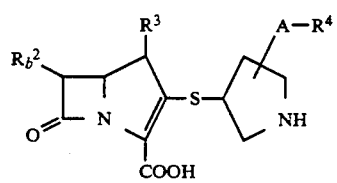

in which $R^2_b$, $R^3$, $R^4$ and A are each as defined above, and pharmaceutically acceptable salts thereof.

Particularly, the compound (I) possessing the most potent antimicrobial activity can be represented by the following formula:

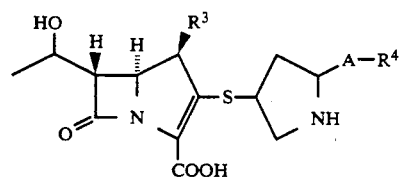

in which $R^3$, $R^4$ and A are each as defined above, and pharmaceutically acceptable salts thereof.

Now in order to show the utility of the object compound (I), the test data on antimicrobial activity of the representative compound of the compound (I) of this invention is shown in the following.

in vitro Antimicrobial Activity

Test Method :

in vitro Antimicrobial Activity was determined by the two-fold agar-plate dilution method as described blow.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of µg/ml after incubation at 37° C. for 20 hours.

Test Compound :

The compound of Example 1-3).

Test Result :

| Test Strain | MIC (µg/ml) |
|---|---|
| P. aeruginosa 2 | 0.39 |

For therapeutic administration, the object compound (I) and the pharmaceutically acceptable salts thereof of the present invention are used in the form of conventional pharmaceutical preparation which contains said compound, as an active ingredient, in admixture with pharmaceuticallyly acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, the kind of diseases, the type of compound (I) to be applied, etc. In general, an amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compound (I) of the present invention may be used in treating diseases involving infection by pathogenic microorganisms.

The following Preparations and Examples are given for the purpose of illustrating this invention in more detail and are not intended to be limiting thereof.

Preparation 1-1)

To a mixture of N,N-dimethylformamide (1.20 ml) and tetrahydrofuran (2.4 ml) was added dropwise phosphorus oxychloride (1.25 ml) at −20° C. and the mixture was stirred at 5° C. for 5 minutes. To the mixture was added a solution of (2S,4R)-4-methanesulfonyloxy-1-(4-nitrobenzyloxycarbonyl)proline (4.0 g) in tetrahydrofuran (10 ml) under ice-cooling. The mixture was stirred at the same temperature for 30 minutes. To a solution of 4,5,6,7-tetrahydropyrazolo[1,5-a]pyrimidine (1.40 g) in tetrahydrofuran (20 ml) and water (10 ml) was added dropwise the solution obtained above with stirring under ice-cooling, keeping the pH to 8–10 with triethylamine. The mixture was stirred at the same condition for 1 hour. To the reaction mixture was added ethyl acetate (100 ml) and the organic layer was washed with saturated aqueous sodium hydrogen carbonate and saturated aqueous sodium chloride successively, dried over anhydrous magnesium sulfate and evaporated in vacuo. The resulting residue was chromatographed on silica gel (100 g) eluting with a mixture of chloroform and methanol (19:1, V/V). The fractions containing the desired compound were collected and evaporated in vacuo to give (2S,4R)-4-methanesulfonyloxy-1-(4-nitrobenzyloxycarbonyl)-2-{4,5,6,7-tetrahydropyrazolo [1,5-a]pyrimidin-4-yl)carbonylpyrrolidine (3.84 g).

NMR (CDCl$_3$δ) : 2.11–2.80 (4H, m), 3.07 (3H, s), 4.85–5.43 (4H, m), 7.25–7.48 (1H, br s), 7.45 (1H, bd, J=9.1Hz), 7.50 (1H, bd, J=8.6Hz), 8.22 (2H, d, J=6.9Hz)

Preparation 1-2)

To a solution of sodium borohydride (0.88 g) in tetrahydrofuran (40 ml) was added dropwise boron trifluoride ether complex (15.3 ml) under ice-cooling and the suspension was stirred at the same temperature for 10 minutes. To the mixture was added a solution of (2S,4R)-4-methanesulfonyloxy-1-(4-nitrobenzyloxycarbonyl)-2-{4,5,6,7-tetrahydropyrazolo [1,5-a]pyrimidin-4-yl}-carbonylpyrrolidine (3.83 g) in tetrahydrofuran (20 ml) and the mixture was stirred at the same temperature overnight. Methanol (20 ml) was added dropwise to the reaction mixture and the solution was filtered. The filtrate was evaporated in vacuo. The resulting residue was chromatographed on silica gel (150 g) eluting with a mixture of chloroform and methanol (19:1, V/V). The fractions containing the desired compound were collected and concentrated in vacuo to give (2S,4R)-4-methanesulfonyloxy-1-(4-nitrobenzyloxycarbonyl)-2-{4,5,6,7-tetrahydropyrazolo [1,5-a]pyrimidin-4-yl}methylpyrrolidine (2.66 g).

NMR (CDCl$_3$δ) : 2.05–2.30 (3H, m), 2.34–2.58 (1H, m), 3.03 (3H, s), 3.18–3.73 (5H, m), 3.92–4.15 (3H, m), 4.23–4.38 (1H, m), 5.10–5.40 (4H, m), 7.20 (1H, br s), 7.52 (2H, bd, J=8.2Hz), 8.22 (2H, d, J=8.7Hz)

Preparation 1-3)

To a solution of sodium hydride (60% suspension in oil, 0.27 g) in N,N-dimethylformamide (15 ml) was added dropwise thioacetic S-acid (0.51 ml) with stirring under ice-cooling. The mixture was stirred at the same temperature for 30 minutes. A solution of (2S,4R)-4-methanesulfonyloxy-1-(4-nitrobenzyloxycarbonyl)-2-{4,5,6,7-tetrahydropyrazolo [1,5-a]pyrimidin-4-yl)methylpyrrolidine (2.65 g) in N,N-dimethylformamide (15 ml) was added to the mixture obtained above with stirring at the same temperature and the mixture was stirred at 80°~90° C. for 2 hours. The reaction mixture was poured into ice-water (100 ml) and extracted twice with ethyl acetate (100 ml). The extract was washed with saturated aqueous sodium chloride, dried over anhydrous magnesium sulfate and evaporated in vacuo. The resulting residue was chromatographed on silica gel (150 g) eluting with a mixture of chloroform and methanol (19:1, V/V). The fractions containing the desired compound were collected and evaporated in vacuo to give (2S,4S)-4-acetylthio-1-(4-nitrobenzyloxycarbonyl) -2-{4,5,6,7-tetrahydropyrazolo-[1,5-a]pyrimidin-4-yl}methylpyrrolidine (2.23 g).

NMR (CDCl$_3$δ) : 1.70–1.96 (1H, m), 2.00–2.20 (2H, m), 2.36 (3H, s), 2.44–3.70 (1H, m), 5.10–5.55 (3H, m), 7.23 (1H, br s), 7.49 (2H, bd, J=7.9Hz), 8.23 (2H, d, J=8.6Hz)

Preparation 1-4)

To a solution of (2S,4S)-4-acetylthio-1-(4-nitrobenzyloxycarbonyl) -2-{4,5,6,7-tetrahydropyrazolo [1,5-a]pyrimidin-4-yl}methylpyrrolidine (2.22 g) in a mixture of methanol (40 ml) and tetrahydrofuran (20 ml) was added 28% sodium methoxide in methanol solution (0.98 ml) under ice-cooling and the mixture was stirred at the same temperature for 15 minutes. To the reaction mixture was added acetic acid (0.29 ml) at the same temperature and the mixture was evaporated in vacuo. The resulting residue was dissolved in a mixture of ethyl acetate (100 ml) and water (30 ml). The organic layer was separated and washed with saturated aqueous sodium chloride, dried over anhydrous magnesium sulfate and concentrated in vacuo. The resulting residue was chromatographed on silica gel (150 g) eluting with a mixture of chloroform and methanol (19:1, V/V). The fractions containing the desired compound were collected and concentrated in vacuo to give (2S,4S)-4-mercapto-1-(4-nitrobenzyloxycarbonyl) -2-{4,5,6,7-tetrahydropyrazolo[1,5-a]pyrimidin-4-yl}methylpyrrolidine (1.80 g).

NMR CDCl$_3$δ) : 1.70–1.95 (1H, m), 2.06–2.22 (2H, m), 2.36 (1H, s), 2.43–2.65 (1H, m), 3.06–3.80 (6H, m), 3.85–4.30 (4H, m), 5.10–5.55 (3H, m), 7.25 (1H, br s), 7.50 (2H, d, J=8.1Hz), 8.22 (2H, d, J=8.7Hz)

Preparation 2-1)

2S,4R)-2-(2,3-Dihydro-1H-imidazo[1,2-b]pyrazol-1-yl) -carbonyl-4-methanesulfonyloxy-1-(4-nitrobenzyloxycarbonyl)pyrrolidine was obtained in 82.1% yield in substantially the same manner as that of Preparation 1-1).

NMR (CDCl$_3$δ) : 2.25–2.53 (1H, m), 2.66–2.83 (1H, m), 3.09 (3H, s), 3.86–4.10 (2H, m), 4.14–4.76 (4H, m), 4.93–5.15 (1H, m), 5.20–5.48 (3H, m), 5.75, 6.14 (1H, each s), 7.27–7.57 (3H, m), 8.06–8.30 (2H, m)

Preparation 2-2)

(2S,4R)-2-(2,3-Dihydro-1H-imidazo[1,2-b]pyrazol-1-yl) -methyl-4-methanesulfonyloxy-1-(4-nitrobenzyloxycarbonyl)pyrrolidine was obtained in 84.8% yield in substantially the same manner as that of Preparation 1-2).

NMR (CDCl$_3$δ) : 2.20–2.66 (2H, m), 3.05 (3H, s), 3.20–4.34 (9H, m), 5.16 (1H, br s), 5.22–5.38 (3H, br s), 7.29 (1H, s), 7.53 (2H, d, J=8.7Hz), 8.22 (2H, m)

Preparation 2-3)

(2S,4S)-4-Acetylthio-2-(2,3-dihydro-1H-imidazo-[1,2-b]pyrazol-1-yl)methyl-1-(4-nitrobenzyloxycarbonyl)pyrrolidine was obtained in 97.6% yield in substantially the same manner as that of Preparation 1-3).

NMR (CDCl$_3$δ) : 1.86–2.12 (1H, m), 2.35 (3H, s), 2.48–2.72 (1H, m), 3.15–3.46 (3H, m), 3.66–4.24 (7H, m), 5.23 (3H, br s), 7.31 (1H, d, J=1.8Hz), 7.52 (2H, d. J=8.8Hz), 8.23 (2H, d. J=8.7Hz)

Preparation 2-4)

(2S,4S)-2-(2,3-Dihydro-1H-imidazo[1,2-b]pyrazol-1-yl) methyl-4-mercapto-1-(4-nitrobenzyloxycarbonyl)-pyrrolidine was obtained in 65.9% yield in substantially the same manner as that of Preparation 1-4).

IR (Neat) : 1710–1700, 1690, 1610, 1575, 1525, 1425, 1405, 1350 cm$^{-1}$

NMR (CDCl$_3$δ) : 1.79 (1H, d, J=6.6Hz), 1.84–2.02 (1H, m), 2.50–2.72 (1H, m), 3.08–3.52 (4H, m), 3.65–3.92 (2H, m), 3.98–4.28 (4H, m), 5.23 (3H, br s), 7.31 (1H, d, J=1.8Hz), 7.52 (2H, d, J=8.8Hz), 8.22 (2H, d, J=8.7Hz)

Preparation 3-1)

To a solution of imidazo[1,2-b]pyrazole (1.75 g) in N,N-dimethylformamide (20 ml) was added portionwise sodium hydride (60% in oil suspension, 686 mg) with stirring under ice-cooling. The mixture was stirred at the same temperature for 30 minutes. To a solution of (2S,4R)-1-allyloxycarbonyl-4-tert-butyldimethylsilyloxy-2-(methanesulfonyloxy) methylpyrrolidine (5.0 g) in N,N-dimethylformamide (50 ml) was added the solution obtained above and the mixture was stirred at 80°–90° C. for 2 hours. The reaction mixture was poured into ice-water (100 ml) and extracted twice with ethyl acetate (150 ml). The extract was washed with saturated aqueous sodium chloride, dried over anhydrous magnesium sulfate and evaporated in vacuo. The resulting residue was chromatographed on silica gel (100 g) eluting with a mixture of dichloromethane and acetone (3:1, V/V). The fractions containing the desired compound were collected and evaporated in vacuo to give (2S,4R)-1-allyloxycarbonyl -4-tert-butyldimethylsilyloxy-2-(imidazo[1,2-b]-pyrazol-1-yl) -1-yl)methylpyrrolidine [4.24 g].

NMR (CDCl$_3$δ) : −0.04 (6H, s), 0.80 (9H, s), 1.79–1.95 (2H, m), 3.17–3.42 (2H, m), 3.80–4.46 (4H, m), 4.66 (2H, d, J=5.4Hz), 5.20–5.39 (2H, m), 5.61 (1H, d, J=1.8Hz), 5.87–6.07 (1H, m), 6.64 (1H, s), 7.30–7.41 (2H, m), 7.59 (1H, s)

Preparation 3-2)

A solution of (2S,4R)-1-allyloxycarbonyl-4-tertbutyldimethylsilyloxy-2-(imidazo[1,2-b]pyrazol-1-yl)methylpyrrolidine (4.23 g) and conc. hydrochloric acid (2.61 ml) in methanol (40 ml) was stirred at ambient temperature for 5 hours. The reaction mixture was adjusted to pH 8–9 with 28% sodium methoxide in methanol solution and the mixture was concentrated in vacuo. The resulting residue was chromatographed on silica gel (100 g) eluting with a mixture of dichloromethane and acetone (2:1, V/V). The fractions containing the desired compound were collected and evaporated in vacuo to give (2S,4R)-1-allyloxycarbonyl-4-hydroxy-2-(imidazo [1,2-b]pyrazol-1-yl)methylpyrrolidine (3.18 g).

NMR (CDCl$_3$δ) : 1.76–2.18 (3H, m), 3.24 (1H, dd, J=4.5Hz, J=11.8Hz), 3.45–3.68 (1H, m), 4.00–4.50 (4H, m), 4.65 (2H, d, J=5.6Hz), 5.17–5.40 (2H, m), 5.61 (1H, d, J=2Hz), 5.89–6.04 (1H, m), 6.65 (1H, s), 7.27 (1H, s), 7.58 (1H, s)

Preparation 3-3)

To a solution of (2S,4R)-1-allyloxycarbonyl-4-hydroxy-2-(imidazo[1,2-b]pyrazol-1-yl)methylpyrrolidine (3.16 g) in a mixture of ethyl acetate (60 ml) and triethylamine (2.27 ml) was dropwise added a solution of methanesulfonyl chloride (1.18 ml) in ethyl acetate (5 ml) with stirring under ice-cooling. The mixture was stirred at the same temperature for 1 hour. To the reaction mixture was added water (50 ml) with stirring and the organic layer was separated. The organic layer was washed in turn with saturated aqueous sodium chloride, saturated aqueous sodium hydrogen carbonate and saturated aqueous sodium chloride, dried over anhydrous magnesium sulfate and evaporated in vacuo to give a residue. The residue was chromatographed on silica gel (60 g) eluting with a mixture of dichloromethane and acetone (2:1, V/V). The fractions containing the desired compound were collected and evaporated in vacuo to give (2S,4R)-1-allyloxycarbonyl -2-(imidazo[1,2-b]pyrazol-1-yl)methyl-4-methanesulfonyloxypyrrolidine (3.06 g).

NMR (CDCl$_3$δ) : 1.98–2.17 (1H, m), 2.32–2.50 (1H, m), 2.98 (3H, s), 3.23–3.36 (1H, m), 3.80–4.55 (4H, m), 4.68 (2H, m), 4.91 (1H, br s), 5.19–5.42 (2H, m), 5.61 (1H, d, J=1.9Hz), 5.87–6.07 (1H, m), 6.64 (1H, s), 7.31–7.39 (1H, m), 7.61 (1H, s)

Preparation 3-4)

A solution of (2S,4R)-1-allyloxycarbonyl-2-(imidazo [1,2-b]pyrazol-1-yl)methyl-4-methanesulfonyloxypyrrolidine (3.04 g) and potassium thioacetate (1.41 g) in acetonitrile (60 ml) was stirred under refluxing for 4 hours. To the reaction mixture were added ethyl acetate (100 ml) and aqueous sodium chloride (50 ml) with stirring and then the organic layer was separated. The organic layer was washed with saturated aqueous sodium chloride, dried over anhydrous magnesium sulfate and evaporated in vacuo. The resulting residue was chromatographed on silica gel (100 g) eluting with a mixture of dichloromethane and acetone (5:1, V/V). The fractions containing the desired compound were collected and evaporated in vacuo to give (2S,4S)-4-acetylthio-1-allyloxycarbonyl -2-(imidazo[1,2-b]pyrazol-1-yl)methylpyrrolidine (2.33 g).

NMR (CDCl$_3$, δ) : 1.71–1.85 (1H, m), 2.33 (3H, s), 2.34–2.56 (1H, m), 2.96–3.30 (1H, m), 3.80–4.35 (5H, m), 4.63 (2H, d, J=5.5Hz), 5.15–5.39 (2H, m), 5.66 (1H, br s), 5.86–6.10 (1H, m), 6.68 (1H, br s), 7.31 (1H, d, J=1.6Hz), 7.61 (1H, br s)

EXAMPLE 1-1)

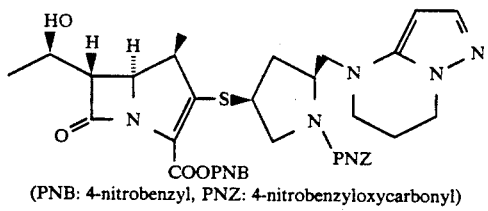

(PNB: 4-nitrobenzyl, PNZ: 4-nitrobenzyloxycarbonyl)

To a solution of 4-nitrobenzyl (4R)-2-diazo-4-[(2R,3S)-3-{(1R)-1-hydroxyethyl}-4-oxoazetidin-2-yl]-3-oxopentanoate (1.00 g) in 1,2-dichloroethane (10 ml) was added rhodium(II) octanoate (10 mg) under refluxing. After refluxing for 30 minutes, the reaction mixture was cooled and evaporated in vacuo to give a residue. The residue was dissolved in benzene (5 ml) and evaporated. This operation was repeated once again and the residue was dried in vacuo to give 4-nitrobenzyl (4R,5R,6S)-6-[(1R)-1-hydroxyethyl]-4-methyl-3,7-dioxo-1-azabicyclo[3.2.0]-heptane-2-carboxylate. The compound obtained was dissolved in acetonitrile (10 ml) and cooled to 0°~2° C. under atmosphere of nitrogen. To this solution were added diphenyl phosphorochloridate (0.56 ml) and N,N-diisopropyl-N-ethylamine (0.49 ml) successively and the mixture was stirred at 0° C. for 40 minutes. To the resulting solution were added dropwise a solution of (2S,4S)-4-mercapto-1-(4-nitrobenzyloxycarbonyl)-2-{4,5,6,7-tetrahydropyrazolo [1,5-a]pyrimidin-4-yl}-methylpyrrolidine (1.62 g) in acetonitrile (5 ml) and N,N-diisopropyl-N-ethylamine (0.77 ml) with stirring at 0°~2° C. and the mixture was stirred at the same temperature for 3 hours. To the reaction mixture was added ethyl acetate (80 ml) and the solution was washed with water and saturated aqueous sodium chloride successively, dried over anhydrous magnesium sulfate and evaporated in vacuo. The resulting residue was chromatographed on silica gel (150 g) eluting with a mixture of dichloromethane and acetone 1, V/V). The fractions containing the desired compound were collected and concentrated in vacuo to give 4-nitrobenzyl (4R,5S,6S)-6-[(1R)-1-hydroxyethyl]-4-methyl-3-[(2S,4S) -1-(4-nitrobenzyloxycarbonyl)-2-{4,5,6,7-tetrahydropyrazolo [1,5-a]pyrimidin-4-yl}methyl pyrrolidin-4-yl]thio-7-oxo-1-azabicyclo[3,2,0]hept-2-ene-2-carboxylate (0.79 g).

IR (Nujol) : 1770–1760, 1720–1670, 1530–1520, 1345 cm$^{-1}$

NMR (90MHz, CDCl$_3$, δ) : 1.17–1.47 (6H, m), 1.71–2.17 (4H, m), 2.43–2.75 (2H, m), 5.10–5.73 (5H, m), 7.17–7.32 (2H, m), 7.33 (2H, d, J=8.5Hz), 7.63 (2H, d, J=8.5Hz), 8.23 (4H, d, J=8.5Hz)

EXAMPLE 1-2

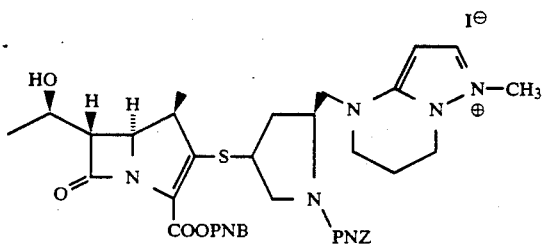

To a solution of 4-nitrobenzyl (4R,5S,6S)-6-[(1R)-1-hydroxyethyl]-4-methyl-3-[(2S,4S)-1-(4-nitrobenzyloxycarbonyl) -2-{4,5,6,7-tetrahydropyrazolo[1,5-a]pyrimidin-4yl}methylpyrrolidin-4-yl]thio-7-oxo-1-azabicyclo[3.2.0]-hept-2-ene-2-carboxylate (0.78 g) in a mixture of acetone (8 ml) and tetrahydrofuran (16 ml) was added methyl iodide (0.64 ml) with stirring and the mixture was allowed to stand at ambient temperature overnight. The reaction mixture was evaporated in vacuo to give 4-nitrobenzyl (4R,5S,6S)-6-[(1R)-1-hydroxyethyl]-4-methyl-3-[(2S,4S)-1-(4-nitro benzyloxycarbonyl)-2-{1-methyl-4,5,6,7-tetrahydro-4-pyrazolo [1,5-a]primidinio}methylpyrrolidin-4yl]thio-7-oxo-1-azabicyclo[3.2.0]hept-2-ene-2-carboxylate iodide (0.88 g).

This compound was immediately used as the starting compound for the next step.

EXAMPLE 1-3

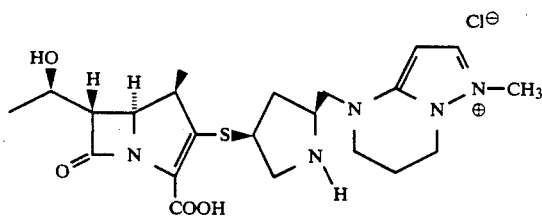

A solution of 4-nitrobenzyl (4R,5S,6S)-6-[(1R)-1-hydroxyethyl]-4-methyl-3-[(2S,4S)-1-(4-nitrobenzyloxycarbonyl) -2-{1-methyl-4,5,6,7-tetrahydro-4-pyrazolo-[1,5-a]pyrimidinio}methylpyrrolidin-4-yl]thio-7-oxo-1-azabicyclo [3.2.0]hept-2-ene-2-carboxylate iodide (0.88 g), 20% palladium hydroxide on carbon (0.5 g), 01 M phosphoric acid buffer (pH=5.6, 35 ml), and tetrahydrofuran (35 ml) was stirred for 5 hours under atmospheric pressure of hydrogen at ambient temperature. After the catalyst was filtered off, the filtrate was evaporated in vacuo to remove the organic solvent. The aqueous layer was washed twice with ethyl acetate (50 ml) and evaporated in vacuo to remove the organic solvent. The residue was chromatographed on a nonionic adsorption resin "Diaion HP-20" (trademark, made by Mitsubishi Chemical Industries) (30 ml) eluting in turn with water (90 ml) and 5% aqueous acetone (150 ml). The fractions containing the desired compound were collected and concentrated in vacuo. The residue was dissolved in water (30 ml) and the solution was passed through an ion exchange resin "Amberlist A-26" (Cl$^-$ type) (Trademark, made by Rohm & Haas Co., Ltd.) (5 ml) and eluted with water (100 ml). The eluates were evaporated in vacuo and lyophilized to give (4R, 5S,6S)-6-[(1R)-1-hydroxyethyl]-4-methyl-3-[(2 S,4S)-2-{1-methyl-4,5,6,7-tetrahydro-4-pyrazolo[1,5-a]pyrimidinio}methylpyrrolidin-4-yl]thio-7-oxo-1-azabicyclo[3.2.0]-hept-2-ene-2-carboxylic acid chloride (0.35 g).

mp : >160° C. (dec)

IR (Nujol) : 1755–1720, 1610–1560 cm$^{-1}$

NMR (90MHz, D20, 6) : 1.20 (3H, d, J=7Hz), 1.28 (3H, d, J=6Hz), 1.50–1.91 (1H, m), 2.08–2.41 (2H, m), 2.51–2.93 (1H, m), 3.78 (3H, s), 5.95 (1H, d, J=4Hz), 7.67 (1H, d, J=4Hz)

FAB Mass : 462 (M$^+$-1)

EXAMPLE 2-4 1

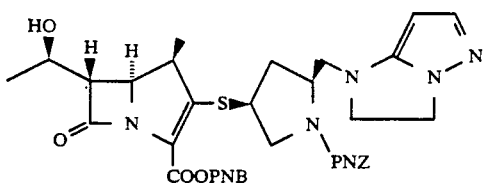

4-Nitrobenzyl (4R,5S,6S)-3-[(2S,4S)-2-(2,3-dihydro-1H-imidazo [1,2-b]pyrazol-1-yl)methyl-1-(4-nitrobenzyloxycarbonyl) pyrrolidin-4-yl]thio-6-[(1R)-1-hydroxyethyl]-4-methyl-7-oxo-1-azabicyclo [3.2.0]hept-2-ene-2-carboxylate was obtained in 56.3% yield in substantially the same manner as that of Example 1-1).

NMR (90MHz, CDCl₃, δ) : 1.28 (3H, d, J=6Hz), 1.35 (3H, d, J=7Hz), 1.55-1.80 (2H, m), 3.09-4.39 (10H, m), 5.08-5.65 (5H, m), 7.22-7.33 (2H, m), 7.50 (2H, d, J=7Hz), 7.62 (2H, d, J=9Hz), 8.20 (4H, d, J=9Hz)

Example 2-2

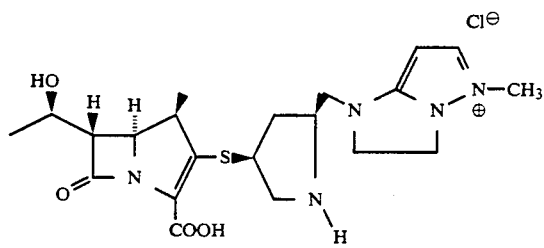

To a solution of 4-nitrobenzyl (4R,5S,6S)-3-[(2S,4S)-2-(2,3-dihydro-1H-imidazo[1,2-b]pyrazol-1-yl)methyl-1-(4-nitrobenzyloxycarbonyl) pyrrolidin-4-yl]thio-6-[(1R)-1hydroxyethyl]-4-methyl-7-oxo-1-azabicyclo[3.2.0]hept-2-ene-2-carboxylate (1.02 g) in acetone (20 ml) was added methyl iodide (3.4 ml) with, stirring and the mixture was allowed to stand at ambient temperature overnight. The reaction mixture was evaporated in vacuo to give a residue. A solution of the residue, 20% palladium hydroxide on carbon (0.5 g), 01 M phosphoric acid buffer (pH=5.8, 50 ml), and tetrahydrofuran (50 ml) was stirred for 5 hours under atmospheric pressure of hydrogen at ambient temperature. After the catalyst was filtered off, the filtrate was evaporated in vacuo to remove the organic solvent. The aqueous layer was washed twice with ethyl acetate (50 ml) and evaporated in vacuo to remove the organic solvent. The residue was chromatographed on a nonionic adsorption resin "Diaion HP-20" (30 ml) eluting in turn with water (60 ml) and 5% aqueous acetone (180 ml). The fractions containing the desired compound were collected and concentrated in vacuo. The residue was dissolved in water (30 ml) and the solution was passed through an ion exchange resin "Amberlist A-26" (Cl⁻ type) (6 ml) and eluted with water (100 ml). The eluates were evaporated in vacuo and lyophilized to give (4R,5S,6S)-3-[(2S,4S) -2-(5-methyl-2,3-dihydro-1H-1-imidazo[1,2-b]-pyrazolio) methylpyrrolidin-4-yl]thio-6-[(1R)-1-hydroxyethyl]-4-methyl-7-oxo-1-azabicyclo[3.2.0]hept-2-ene-2-carboxylic acid chloride (0.40 g).

IR (Nujol) : 1760-1740, 1590-1560 cm⁻¹

NMR (90MHz, D20, 6) : 1.20 (3H, d, J=7Hz), 1.28 (3H, d, J=6Hz), 1.50-1.93 (1H, m), 2.46-2.91 (1H, m), 3.20-3.61 (6H, m), 3.79 (3H, s), 3.80-4.54 (7H, m), 5.91 (1H, d, J=3Hz), 7.76 (1H, d, J=3Hz)

FAB Mass : 448 (M+)

EXAMPLE 2-3

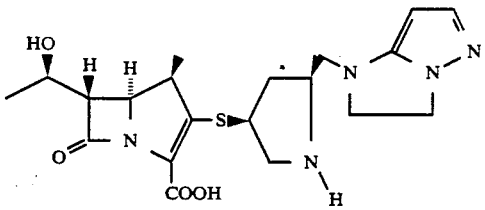

A solution of 4-nitrobenzyl (4R,5S,6S)-3-[(2S,4S)-2-(2,3-dihydro-1H-imidazo[1,2-b]pyrazol-1-yl)methyl-1-(4-nitrobenzyloxycarbonyl) pyrrolidin-4-yl]thio-6-[(1R)-1-hydroxyethyl]-4-methyl-7-oxo-1-azabicyclo[3.2.0]hept-2-ene-2-carboxylate (0.70 g), 20% palladium hydroxide on carbon (0.4 g), 01 M phosphoric acid buffer (pH=6.0, 35 ml) and tetrahydrofuran (35 ml) was stirred for 5 hours under atmospheric pressure of hydrogen at ambient temperature. After the catalyst was filtered off, the filtrate was evaporated in vacuo to remove the organic solvent. The aqueous layer was washed twice with ethyl acetate (30 ml) and evaporated in vacuo to remove the organic solvent. The residue was chromatographed on a nonionic adsorption resin "Diaion HP-20" (20 ml) eluting in turn with water (60 ml) and 5% aqueous acetone [120 ml). The fractions containing the desired compound were collected and lyophilized to give (4R,5S,6S)-3-[(2S,4S)-2-(2,3-dihydro-1H-imidazo[1,2-b]pyrazol-1-yl)methylpyrrolidin-4-yl ]thio-6-[(1R)-1-hydroxyethyl]-4-methyl-7-oxo-1-azabicyclo [3.2.0]hept-2-ene-2-carboxylic acid (0.29 g).

IR (Nujol) : 1755, 1565 cm⁻¹

NMR (90MHz, D20, 6) : 1.20 (3H, d, J=8Hz), 1.27 (3H, d, J=7Hz), 1.51-1.96 (1H, m), 2.44-2.96 (1H, m), 5.52 (1H, d, J=2Hz), 7.34 (1H, d, J=2Hz)

FAB Mass : 434 (M+)

EXAMPLE 3-1

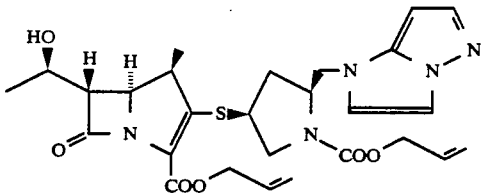

To a solution of allyl (4R)-2-diazo-4-[(2R,3S)-3-{(1R)-1-hydroxyethyl}-4-oxoazetidin-2-yl]-3-oxopentanoate (1.41 g) in ethyl acetate (14 ml) was added rhodium(II) octanoate (19 mg) under refluxing in a stream of nitrogen. The mixture was refluxed for 30 minutes and then evaporated in vacuo to give a residue. The residue was dissolved in acetonitrile (15 ml) and cooled at 0-5° C. under an atmosphere of nitrogen. To the solution were added diphenyl phosphorochloridate (1.09 ml) and N,N-diisopropyl-N-ethylamine (0.96 ml) successively and the mixture was stirred at the same condition overnight. On the other hand, to a solution of (2S,4S)-4-acetylthio-1-allyloxycarbonyl-2-(imidazo[1,2-b]-pyrazol-1-yl) methylpyrrolidine (2.33 g) in a mixture of tetrahydrofuran (20 ml) and methanol (20 ml) was added 28% sodium methoxide in methanol solution (1.41 ml) under ice-cooling and the mixture was stirred at the same temperature for 15 minutes. To the reaction mixture was added acetic acid (0.42 ml) and the mixture was evaporated in vacuo. The resulting residue was dissolved in ethyl acetate (50 ml). The solution was washed with saturated aqueous sodium chloride, dried over anhydrous magnesium sulfate and evaporated in vacuo to give a residue. To the mixture obtained above were added a solution of this residue in acetonitrile (10 ml) and N,N-diisopropyl-N-ethylamine (1.25 ml) successively under ice-cooling and the mixture was stirred at the same temperature for 2 hours. To a reaction mixture were added ethyl acetate (100 ml) and water (50 ml) with stirring and separated. The organic layer was washed with saturated aqueous sodium chloride, dried over anhydrous magnesium sulfate and evaporated in vacuo. The resulting residue was chromatographed on silica gel (100 g) eluting with a mixture of dichloromethane and acetone (2:1, V/V). The fractions containing the desired compound were collected and evaporated in vacuo to give allyl (4R,5S,6S)-3-[(2S,4S) -1-allyloxycarbonyl-2-(imidazo[1,2-b]pyrazol-1-yl) methylpyrrolidin-4-yl]thio-6-[(1R)-1-hydroxyethyl]-4-methyl-7-oxo-1-azabicyclo [3.2.0]hept-2-ene-2-carboxylate (1.66 g).

IR (Nujol) : 1760, 1700 (sh), 1690, 1590 cm$^{-1}$

NMR (CDCl$_3$δ) : 1.17 (3H, d, J=6.8Hz), 1.36 (3H, d, J=6.2Hz), 1.66-1.82 (1H, m), 2.30-2.55 (1H, m), 2.75-3.65 (5H, m), 3.60-4.40 (6H, m), 4.55-4.90 (4H, m), 5.20-5.50 (4H, m), 5.72 (1H, br s), 5.80-6.10 (2H, m), 6.72 (1H, s), 7.33 (1H, d, J=2.1Hz), 7.62 (1H, dd, J=1.2Hz, J=2.2Hz)

EXAMPLE 3-2

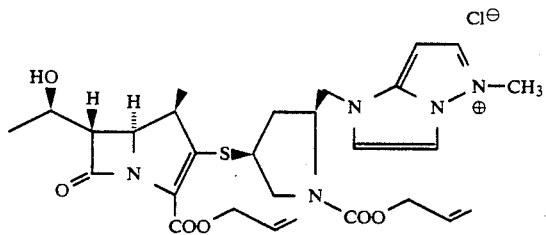

A solution of allyl (4R,5S,6S)-3-[(2S,4S)-1-allyloxycarbonyl-2-(imidazo [1,2-b]pyrazol-1-yl)-methylpyrrolidin-4-yl]thio-6-[(1R)-1-hydroxyethyl]-4-methyl-7-oxo-1-azabicyclo [3.2.0]hept-2-ene-2-carboxylate (1.64 g) and methyl iodide (1.84 ml) in acetone (20 ml) was stirred at ambient temperature for 30 minutes and then allowed to stand at the same temperature overnight. The reaction mixture was evaporated in vacuo and dried in vacuo for 1 hour to give allyl (4R,5S,6S)-3-[(2S,4S)-1-allyloxycarbonyl-2-(5-methylimidazo [1,2-b]-1-pyrazolio)methylpyrrolidin-4-yl]thio-6-[(1R)-1-hydroxyethyl]-4-methyl-7-oxo-1-azabicyclo [3.2.0]hept-2-ene-2-carboxylate iodide (2.09 g).

IR (Neat) : 1760, 1705 1690, 1595 cm$^{-1}$

NMR (CDCl$_3$δ) : 1.24 (3H, d, J=6Hz), 1.35 (3H, d, J=6.3Hz), 1.70-1.90 (1H, m), 2.72-2.90 (1H, m), 3.25-3.40 (3H, m), 4.15-4.33 (5H, m), 4.34 (3H, s), 4.50-4.82 (6H, m), 5.20-5.50 (4H, m), 5.80-6.05 (2H, m), 6.60 (1H, d, J=3.5Hz), 7.51 (1H, br s), 8.04 (1H, d, J=3.5Hz), 8.15 (1H, d, J=2.3Hz)

EXAMPLE 3-3

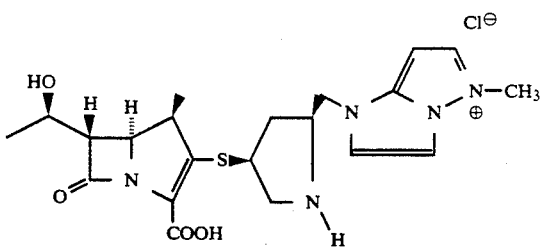

To a solution of allyl (4R,5S,6S)-3-[(2S,4S)-1-allyloxycarbonyl -2-(5-methylimidazo[1,2-b]-1-pyrazolio)methylpyrrolidin-4-yl]thio-6-[(1R)-1-hydroxyethyl]-4-methyl-7-oxo-1-azabicyclo [3.2.0]hept-2-ene-2-carboxylate iodide (1.0 g), triphenylphosphine (38 mg) and morpholine (0.31 ml) in a mixture of tetrahydrofuran (8 ml) and ethanol (8 ml) was added tetrakis(triphenylphosphine)palladium (0) (33 mg) at ambient temperature in a stream of nitrogen. The mixture was stirred at the same condition for 2 hours. The resulting precipitates were collected by filtration, washed with tetrahydrofuran and dichloromethane successively, and dried in vacuo at ambient temperature for 3 hours. The precipitates were dissolved in water (10 ml) and chromatographed on nonionic adsorption resin, "Diaion HP-20" (Trademark, made by Mitsubishi Chemical Industries) (30 ml) eluting in turn with water (60 ml) and 5% aqueous acetone (90 ml). The fractions containing the desired compound were collected and concentrated in vacuo. The resulting residue (about 20 ml) was passed through ion exchange resin, "Amberlyst A-26" (Cl$^-$ type, trademark, made by Rohm and Haas Co., Ltd.) (10 ml) and eluted with water (20 ml). The eluate was lyophilized to give (4R,5S,6S)-6-[(1R)-1-hydroxyethyl]-4-methyl-3-[(2S,4S)-2-{5-methylimidazo-[1,2-b]-1-pyrazolio}methylpyrrolidin-4-yl]thio-7-oxo-1-azabicyclo [azablcyclo[3.2.0]hept-2-ene-2-carboxylic acid chloride (334 mg).

IR (Nujol) : 1755-1740, 1590-1580 cm$^{-1}$

NMR (D$_2$O, δ) : 1.23 (3H, d, J=7.2Hz), 1.29 (3H, d, J=6.4Hz), 1.70-1.93 (1H, m), 2.70-2.91 (1H, m), 3.30-3.50 (3H, m), 3.68 (1H, dd, J=6.7Hz), J=12.5Hz), 4.08 (4H, s), 4.20-4.30 (3H, m), 4.63-4.73 (2H, m), 6.54 (1H, d, J=3.5Hz), 7.61 (1H, m), 7.93 (1H, d, J=2.3Hz), 8.00 (1H, d, J=3.5Hz)

FAB Mass : 446.3 (M$^+$)

Obviously, numerous modifications and variations of the present invention are possible in light of the above teachings. It is therefore to be understood that within the scope of the appended claims, the invention may be practiced otherwise than as specifically described herein.

What we claim is:

1. A compound of the formula:

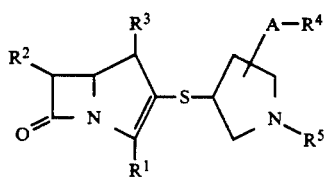

in which $R^1$ is carboxy or protected carboxy, $R^2$ is hydroxy(lower)alkyl or protected hydroxy(lower)alkyl, $R^3$ is hydrogen or lower alkyl, $R^4$ is unsaturated 7 to 12-membered, hererobicyclic group containing 1 to 4 nitrogen atom(s), unsaturated 7 to 12-membered, heterobicyclic group containing 1 to 3 oxygen atom(s), unsaturated 7 to 12-membered, heterobicyclic group containing 1 to 3 sulfur atom(s), unsaturated 7 to 12-membered, heterobicyclic group containing 1 to 3 nitrogen atom(s) and 1 and 2 oxygen atom(s), unsaturated 7 to 12-membered, heterobicyclic group containing 1 to 3 nitrogen atom(s) and 1 to 2 sulfur atom(s), unsaturated 7 to 12-membered, heterobicyclic group containing 1 to 2 oxygen atom(s) and 1 to 2 sulfur atom(s) or unsaturated 7 to 12-membered, heterobicyclic group containing a nitrogen atom, an oxygen atom and a sulfur atom, wherein said heterocyclic group may be substituted by one to three suitable substituent(s) selected from the group consisting of oxo, carboxy(lower)alkyl, protected carboxy(lower)alkyl, amino, protected amino, lower alkylamino, ureido(lower)alkyl, carbamoyl, carbamoyl(lower)alkyl, lower alklyl, lower alkanoyl(lower alkyl, amino(lower)alkyl, protected amino(lower)alkyl, hydroxy(lower)alkyl, protected hydroxy(lower)alkyl, azido(lower)alkyl, halo(lower)alkyl and imino-protective group, $R^5$ is hydrogen or imino-protective group, and A is lower alklylene, or a pharmaceutically acceptable salt thereof.

2. The compound of claim 1, wherein $R^4$ is unsaturated 8 or 9-membered, heterobicyclic group containing 1 to 4 nitrogen atom(s), unsaturated 8 or 9-membered, heterobicyclic group containing 1 to 3 oxygen atom(s), unsaturated 8 or 9-membered, heterobicyclic group containing 1 to 3 nitrogen atom(s) and 1 to 2 oxygen atom(s), unsaturated 8 or 9-membered, heterobicyclic group containing 1 to 3 nitrogen atom(s) and 1 to 2 sulfur atom(s), unsaturated 8 or 9-membered, heterobicyclic group containing 1 to 2 oxygen atom(s) and 1 to 2 sulfur atom(s) or unsaturated 8 or 9-membered, heterobicyclic group containing a nitrogen atom, a oxygen atom and a sulfur atom, wherein said heterocyclic group may be substituted by one to three suitable substituent(s) selected from the group consisting of oxo, carboxy(lower)alkyl, esterified carboxy(lower)alkyl, amino, acylamino, lower alkylamino, ureido(lower)alkyl, carbamoyl, carbamoyl(lower)alkyl, lower alkyl, lower alkanoyl(lower)alkyl, amino(lower)alkyl, acylamino(lower)alkyl, hydroxy(lower)alkyl, acyloxy(lower)alkyl, ar(lower)alkyloxy(lower)alkyl, trisubstituted silyloxy(lower)alkyl, azido(lower)alkyl, halo(lower)alkyl and acyl.

3. The compound of claim 3, wherein $R^1$ is carboxy or esterified carboxy, $R^2$ is hydroxy(lower)alkyl, acyloxy(lower)alkyl, ar(lower)alkyloxy(lower)alkyl or trisubstituted silyloxy(lower)alkyl, $R^5$ is hydrogen or acyl.

4. The compound of claim 3, wherein $R^2$ is hydroxy(lower)alkyl, acyloxy(lower)alkyl, ar(lower)alkyloxy(lower)alkyl, tri(lower)alkylsilyloxy(lower)alkyl, triarylsilyloxy(lower)alkyl or triar(lower)alkylsilyloxy(lower)alkyl.

5. The compound of claim 4, wherein $R^1$ is carboxy, lower alkenyloxycarbonyl or phenyl(or nitrophenyl)(lower)alkoxycarbonyl, $R^2$ is hydroxy(lower)alkyl, phenyl(or nitrophenyl)(lower)alkoxy(lower)alkyl or tri(lower)alkylsilyloxy(lower)alkylsilyloxy(lower)alkyl, $R^4$ is pyrazolopyrimidinyl, tetrahydropyrazolopyrimidinyl, imidazopyrazolyl, dihydro-imidazopyrazolyl, indolizinyl, isoindolyl, 3H-indolyl, indolyl, 1H-indazolyl, indolinyl, isoindolinyl, purinyl, 4H-quinolizinyl, isoquinolyl, quinolyl, phthalazinyl, naphthyridinyl, quinoxalinyl, quinazolinyl, cinnolinyl, pteridinyl, pyradinopyridazinyl, imidazotriazinyl, benzofuranyl, isobenzofuranyl, chromenyl, isochromanyl, chromanyl, benzoxepinyl, cyclopentapyranyl, furopyranyl, dihydrodithianaphthalenyl, dithianaphthalenyl, dioxoloimidazolyl, benzoxazinyl, pyridooxazinyl, pyrazoloxazolyl, imidazothiazolyl, dithiadiazaindanyl, thienofuranyl, oxathiolopyrrolyl, wherein said heterocyclic group may be substituted by one to three suitable substituent(s) selected from the group consisting of oxo, carboxy(lower)alkyl, lower alkenyloxycarbonyl, phenyl(or nitrophenyl)(lower)alkoxycarbonyl, amino, lower alkenyloxycarbonylamino, phenyl(or nitrophenyl)(lower)alkoxycarbonylamino, lower alkylamino, ureido(lower)alkyl, carbamoyl, carbamoyl(lower)alkyl, lower alkyl, lower alkanoyl(lower)alkyl, amino(lower)alkyl, lower alkenyloxycarbonylamino(lower)alkyl, phenyl(or nitrophenyl)(lower)alkoxycarbonylamino(lower)alkyl, hydroxy(lower)alkyl, lower alkenyloxycarbonyloxy(lower)alkyl, phenyl(or nitrophenyl)(lower)alkoxycarbonyloxy(lower) alkyl, mono- or di- or triphenyl(lower)alkyloxy(lower)alkyl, tri(lower)alkylsilyloxy(lower) alkyl, triphenylsilyloxy(lower)alkyl, tribenzylsilyloxy(lower)alkyl, azido(lower)alkyl, halo(lower)alkyl, lower alkenyloxycarbonyl and phenyl(or nitrophenyl)(lower)alkoxycarbonyl, and $R^5$ is hydrogen, lower alkenyloxycarbonyl or phenyl(or nitrophenyl)(lower)alkoxycarbonyl.

6. The compound of claim 5, wherein $R^1$ is carboxy, $R^2$ is hydroxy($C_1$-$C_4$)alkyl, $R^3$ is hydrogen or $C_1$-$C_4$ alkyl, $R^4$ is pyrazolopyrimidinyl, tetrahydropyrazolopyrimidinyl, imidazopyrazolyl, dihydro-imidazopyrazolyl, indolizinyl, isoindolyl, 3H-indolyl, indolyl, 1H-indazolyl, indolinyl, isoindolinyl, purinyl, 4H-quinolizinyl, isoquinolyl, quinolyl, phthalazinyl, naphthyridinyl, quinoxalinyl, quinazolinyl, cinnolinyl, pteridinyl, pyradinopyridazinyl, imidazotriazinyl, benzofuranyl, isobenzofuranyl, chromenyl, isochromanyl, chromanyl, benzoxepinyl, cyclopentapyranyl, furopyranyl, dihydrodithianaphthalenyl, dithianaphthalenyl, dioxoloimidazolyl, benzoxazinyl, pyridooxazinyl, pyrazoloxazolyl, imidazothiazolyl, dithiadiazaindanyl, thienofuranyl, oxathiolopyrrolyl, wherein said heterocyclic group may be substituted by one to three suitable substituent(s) selected from the group consisting of oxo, carboxy($C_1$-$C_4$)alkyl, amino, $C_1$-$C_4$ alkylamino, ureido($C_1$-$C_4$)alkyl, carbamoyl, carbamoyl($C_1$-$C_4$)alkyl, $C_1$-$C_4$ alkyl, $C_1$-$C_4$ alkanoyl($C_1$-$C_4$)alkyl, amino($C_1$-$C_4$)alkyl, hydroxy($C_1$-$C_4$)alkyl, azido($C_1$-$C_4$)alkyl and halo($C_1$-$C_4$)alkyl, $R^5$ is hydrogen, and A is $C_1$-$C_4$ alkylene.

7. The compound of claim 6, wherein $R^2$ is 1-hydroxyethyl, $R^3$ is hydrogen or methyl, $R^4$ is tetrahydropyrazolopyrimidinyl, dihydroimidazopyrazolyl or imidazopyrazolyl, and A is methylene.

8. The compound of claim 7, wherein $R^3$ is methyl, and $R^4$ is 4,5,6,7-tetrahydropyrazolo[1,5-a]pyrimidin-4-yl, 2,3-dihydroimidazo[1,2-b]pyrazol-1-yl or imidazo[1,2-b]pyrazol-1-yl.

9. A pharmaceutical composition comprising, as an active ingredient, a compound of claim 1, in admixture with a pharmaceutically acceptable carrier or excipient.

10. A method for the treatment of infectious diseases caused by pathogenic microorganisms which comprises administering an effective amount of a compound of claim 1 to a human being or animal.

* * * * *